(12) United States Patent
Hadi et al.

(10) Patent No.: US 10,457,987 B2
(45) Date of Patent: Oct. 29, 2019

(54) KITS AND METHODS FOR MULTIPLEX ANALYSIS OF 13 MR Y-STRS

(71) Applicant: University of Central Lancashire, Preston, Lancashire (GB)

(72) Inventors: Sibte Hadi, Preston (GB); Rashed Alghafri, Preston (GB)

(73) Assignee: University of Central Lancashire, Preston, Lancashire (GB)

( * ) Notice: Subject to any disclaimer, the term of this patent is extended or adjusted under 35 U.S.C. 154(b) by 409 days.

(21) Appl. No.: 15/108,011

(22) PCT Filed: Dec. 24, 2014

(86) PCT No.: PCT/GB2014/053844
§ 371 (c)(1),
(2) Date: Jun. 24, 2016

(87) PCT Pub. No.: WO2015/097479
PCT Pub. Date: Jul. 2, 2015

(65) Prior Publication Data
US 2017/0204461 A1 Jul. 20, 2017

(30) Foreign Application Priority Data
Dec. 24, 2013 (GB) .................................. 1323015.6

(51) Int. Cl.
*C12Q 1/68* (2018.01)
*C12Q 1/6876* (2018.01)
(Continued)

(52) U.S. Cl.
CPC ......... *C12Q 1/6876* (2013.01); *C12Q 1/6858* (2013.01); *C12Q 1/6879* (2013.01); *C12Q 2600/156* (2013.01)

(58) Field of Classification Search
None
See application file for complete search history.

(56) References Cited

U.S. PATENT DOCUMENTS

2011/0263437 A1 * 10/2011 Fang .................... C12Q 1/6888
506/7

FOREIGN PATENT DOCUMENTS

WO   WO-2009059049 A1 * 5/2009 ........... C12Q 1/6876
WO   2011032054 A2   3/2011

OTHER PUBLICATIONS

Merriam-Webster, definition of "designate," avail at https://www.merriam-webster.com/dictionary/designate, accessed Feb. 20, 2019.*

(Continued)

*Primary Examiner* — Aaron A Priest
(74) *Attorney, Agent, or Firm* — Burns & Levinson, LLP; Shawn P. Foley (57) ABSTRACT

Provided are methods and kits that allow the amplification, in a single multiplex reaction, of the thirteen rapidly mutating Y chromosome short tandem repeats (RM Y-STRs) at loci DYF387S1; DYF399S1; DYF403S1a/b; DYF404S1; DYS449; DYS518; DYS526a/b; DYS547; DYS570; DYS576; DYS612; DYS626; and DYS627, if present in a sample of DNA, and determination of the alleles at these RM Y-STRs. The ability to achieve such determination through a single multiplex arises as a result of a beneficially designed set of primers disclosed herein. Optimised conditions for the PCR also contribute to the advantages observed. Such kits and methods may be of benefit in the context of forensic sciences.

11 Claims, 7 Drawing Sheets
Specification includes a Sequence Listing.

(51) Int. Cl.
*C12Q 1/6858* (2018.01)
*C12Q 1/6879* (2018.01)

(56) References Cited

OTHER PUBLICATIONS

Dictionary.com, definition of "designate," avail at https://www.dictionary.com/browse/designated, accessed Feb. 20, 2019.*
Kralik et al., A Basic Guide to Real Time PCR in Microbial Diagnostics: Definitions, Parameters, and Everything, Front Microbiol. Feb. 2, 2017;8:108. doi: 10.3389/fmicb.2017.00108. eCollection 2017.*
Ballantyne et al. (Mutability of Y-Chromosomal Microsatellites: Rates, Characteristics, Molecular Bases, and Forensic Implications, Am J Hum Genet. Sep. 10, 2010; 87(3): 341-353).*
Wang et al. (Developmental validation of the AmpF*l* STR® Identifiler® Plus PCR Amplification Kit: an established multiplex assay with improved performance, J Forensic Sci. Mar. 2012;57(2):453-65. doi: 10.1111/j.1556-4029.2011.01963.x. Epub Nov. 10, 2011).*
Mulero et al. (Development and validation of the AmpF*l* STR® MiniFilerTM PCR Amplification Kit: a miniSTR multiplex for the analysis of degraded and/or PCR inhibited DNA. J Forensic Sci 2008;53(4):838-52).*
Accession No. AC163733 (Aug. 3, 2006).*
Accession No. BV208953 (Jul. 16, 2010).*
Alghafri et al. "Rapidly Mutating Y-STRs Multiplex Genotyping Panel to Investigate UAE Population." Forensic Science Int.: Genetics Supplement Series. 4.1(2013):e200-e201.
Ballantyne et al. "A New Future of Forensic Y-chromosome Analysis: Rapidly Mutating Y-STRs for Differentiating Male Relatives and Paternal Lineages." Forensic Science Int.: Genetics. 6.2(2012):208-218.
International Preliminary Report on Patentability issued in International Application No. PCT/GB2014/053844 dated Jun. 28, 2016.
Mulero et al. "Development and Validation of the AmpFlSTRR Yfilertm PCR Amplification Kit: A Male Specific, Single Amplication 17 Y-STR Multiplex System." J. Forensic Sciences. 51.1(2006):64-75.
Thompson et al. "Developmental Validation of the PowerPlex(R) Y23 System: A Single Multiplex Y-STR Analysis System for Casework and Database Samples." Forensic Science Int.: Genetics. 7.2(2013):240-250.

* cited by examiner

KITS AND METHODS FOR MULTIPLEX ANALYSIS OF 13 MR Y-STRS

CROSS REFERENCE TO RELATED APPLICATION

This application is the U.S. national phase entry under 35 U.S.C. § 371 of International Application No. PCT/GB2014/053844, filed Dec. 24, 2014, entitled KITS AND METHODS FOR MULTIPLEX ANALYSIS OF 13 MR Y-STRS, which in turn claims priority to United Kingdom Application No. 1323015.6, filed Dec. 24, 2013, which are incorporated herein by reference in their entirety for all purposes.

The present invention relates to methods and kits for use in determining the alleles of rapidly mutating short tandem repeats located on the Y chromosome.

BACKGROUND

Short tandem repeats (STRs) are commonly used for the analysis of DNA in a range of forensic applications, such as the analysis of DNA found at crime scenes. STRs found on the Y chromosome (Y-STRs) are used in determining the presence of male DNA in samples that may also contain female DNA, such as those obtained in sexual assault cases.

Many Y-STRs are unable to distinguish between related males sharing the same paternal lineage. Since mutations in these Y-STRs are relative rare events, the majority of these will be shared between such male relatives.

Certain Y-STRs have been identified as "rapidly mutating", which for the present purposes indicates that they have mutation rates in the order of $10^{-2}$ whereas all the other Y STRs have a mutation rates in the order of $10^{-3}$. The use of these markers for identification allows distinctions to be made between even closely related male subjects.

SUMMARY OF THE INVENTION

In a first aspect the invention provides a method of determining the alleles of rapidly mutating Y chromosome short tandem repeats (RM Y-STRs) in a sample of interest, the method comprising:
 providing a sample comprising DNA;
 contacting the sample with a set of primers in which each of SEQ ID NO:1 to 26 of Table 2 is present;
 performing polymerase chain reaction (PCR) to co-amplify the RM Y-STRs at loci DYF387S1; DYF399S1; DYF403S1a/b; DYF404S1; DYS449; DYS518; DYS526a/b; DYS547; DYS570; DYS576; DYS612; DYS626; and DYS627 if present in the DNA; and
 comparing the PCR products with reference values representative of different alleles of the RM Y-STRs to determine the alleles present in the sample.

In a second aspect the invention provides a kit comprising a set of primers for the co-amplification of a group of rapidly mutating Y chromosome short tandem repeats (RM Y-STRs), wherein the set of primers comprises each of SEQ ID NOS:1 to 26 set out in Table 2.

In a suitable embodiment of a kit of the second aspect of the invention, the set of primers consists of SEQ ID NOS:1 to 26.

In a third aspect, the invention provides a kit comprising a set of primers for the amplification of a group of rapidly mutating Y chromosome short tandem repeats (RM Y-STRs), wherein the set of primers comprises the group consisting of: SEQ ID NO:1, SEQ ID NO:2, SEQ ID NO:17, SEQ ID NO:18, SEQ ID NO:19, SEQ ID NO:20, SEQ ID NO:21, and SEQ ID NO:22 set out in Table 2.

BRIEF DESCRIPTION OF THE DRAWINGS AND TABLES

Table 1 demonstrates the discriminatory capacity of the RM Y-STRs, co-amplified using the methods of the invention, in a cross sample of UAE population.

Table 2 sets out details of the primer pairs employed in methods and kits of the invention.

DETAILED DESCRIPTION OF THE INVENTION

RM Y-STRs provide tools that are of great benefit in forensic applications. They enable a great deal of discrimination between individual males, even when closely related, due to the almost total absence of haplotype sharing from one individual to another. As a consequence RM Y-STRs, and methods and kits that allow the determination of alleles at these sites, are of great interest and utility in the field of forensic science.

The present invention is based upon the inventors' finding that the primers of SEQ ID NOS:1 to 26, surprisingly, allow effective co-amplification of at least thirteen Y-STRs in a single multiplex PCR reaction. This thirteen-way multiplex reaction is significantly more complex than those that have successfully been practiced in the prior art.

Though other documents have identified the usefulness of the RM Y-STRs that can be amplified using the kits and methods of the invention, none of these have, in practice, been able to produce reagents by which each of the RM Y-STRs can be co-amplified in a single multiplexed reaction. The kits and methods disclosed for the first time in the present application are the first that have been able to achieve this highly desirable aim.

The set of primers set out in Table 2 comprises 13 primer pairs. Each primer pair comprises a forward primer and a reverse primer. Each primer pair is able to amplify a RM Y-STR. Between them the set of primers referred to in the methods of the first aspect of the invention, and kits of the second aspect of the invention, are able to co-amplify the RM Y-STRs found at loci DYF387S1; DYF399S1; DYF403S1a/b; DYF404S1; DYS449; DYS518; DYS526a/b; DYS547; DYS570; DYS576; DYS612; DYS626; and DYS627.

As set out further in Table 2, the primer pair consisting of SEQ ID NOS:1 and 2 is able to amplify the RM Y-STR located at locus DYF387S1; the primer pair consisting of SEQ ID NOS:3 and 4 is able to amplify the RM Y-STR located at locus DYF399S1; the primer pair consisting of SEQ ID NOS:5 and 6 is able to amplify the RM Y-STR located at locus DYF403S1a/b; the primer pair consisting of SEQ ID NOS:7 and 8 is able to amplify the RM Y-STR located at locus DYF404S1; the primer pair consisting of SEQ ID NOS:9 and 10 is able to amplify the RM Y-STR located at locus DYS449; the primer pair consisting of SEQ ID NOS:11 and 12 is able to amplify the RM Y-STR located at locus DYS518; the primer pair consisting of SEQ ID NOS:13 and 14 is able to amplify the RM Y-STR located at locus DYS526a/b; the primer pair consisting of SEQ ID NOS:15 and 16 is able to amplify the RM Y-STR located at locus DYS547; the primer pair consisting of SEQ ID NOS:17 and 18 is able to amplify the RM Y-STR located at locus DYS570; the primer pair consisting of SEQ ID NOS:19 and 20 is able to amplify the RM Y-STR located at locus DYS576; the primer pair consisting of SEQ ID NOS:21 and 22 is able to amplify the RM Y-STR located at locus DYS612; the primer pair consisting of SEQ ID NOS:23 and 24 is able to amplify the RM Y-STR located at locus DYS626; and the primer pair consisting of SEQ ID NOS:25 and 26 is able to amplify the RM Y-STR located at locus DYS627.

The ability to co-amplify each of the RM Y-STRs at DYF387S1; DYF399S1; DYF403S1a/b; DYF404S1; DYS449; DYS518; DYS526a/b; DYS547; DYS570; DYS576; DYS612; DYS626; and DYS627 in a single multiplexed reaction provides a number of significant benefits. Merely by way of example the methods of the invention, or those using the kits of the invention, may be quicker, simpler, and easier than those described in the prior art.

Since the methods and kits of the invention allow co-amplification of thirteen RM Y-STRs in a single multiplex reaction, they reduce the likelihood of contamination that may occur if samples have to be transferred from one reaction vessel to another. The methods and kits o the invention are also able to amplify RM Y-STRs present in male DNA with high specificity, even when the amount of male DNA present in a sample is far less than the amount of female DNA present in the sample. This is of great benefit in the context of forensic samples associated with sexual assaults.

The methods or kits of the invention enable discrimination of individual males to be achieved on the basis of very small quantities of male DNA. As demonstrated in the Examples below, determination of the alleles of RM Y-STRs can be achieved with a starting sample of as little as 65 picograms of male DNA. Since the methods and kits of the invention allow co-amplification of RM Y-STRs in a single multiplex, such small starting samples need not be divided between different reaction mixtures.

The capacity to perform the complex multiplex reactions that can be achieved by the methods and kits of the invention has resulted from the changes to the reaction constituents (in particular the primers of SEQ ID NOS:1 to 26) and conditions that the inventors have made. One of the important parameters that the inventors have identified is the concentrations at which the primers are used. This contributes significantly to the benefits provided by the methods of the invention. In suitable embodiments, concentrations for the various primers may be selected from the group set out below:

SEQ ID NOS:1 and 2 (the primer pair able to amplify the RM Y-STR located at locus DYF387S1) may each be provided at a concentration of between about 0.01 and 1 µM;

SEQ ID NOS:3 and 4 (the primer pair able to amplify the RM Y-STR located at locus DYF399S1) may each be provided at a concentration of between about 0.01 and 1 µM;

SEQ ID NOS:5 and 6 (the primer pair able to amplify the RM Y-STR located at locus DYF403S1a/b) may each be provided at a concentration of between about 0.01 and 1 µM;

SEQ ID NOS:7 and 8 (the primer pair able to amplify the RM Y-STR located at locus DYF404S1) may each be provided at a concentration of between about 0.01 and 1 µM;

SEQ ID NOS:9 and 10 (the primer pair able to amplify the RM Y-STR located at locus DYS449) may each be provided at a concentration of between about 0.01 and 1 µM;

SEQ ID NOS:11 and 12 (the primer pair able to amplify the RM Y-STR located at locus DYS518) may each be provided at a concentration of between about 0.01 and 1 µM;

SEQ ID NOS:13 and 14 (the primer pair able to amplify the RM Y-STR located at locus DYS526a/b) may each be provided at a concentration of between about 0.01 and 1 µM;

SEQ ID NOS:15 and 16 (the primer pair able to amplify the RM Y-STR located at locus DYS547) may each be provided at a concentration of between about 0.01 and 1 µM;

SEQ ID NOS:17 and 18 (the primer pair able to amplify the RM Y-STR located at locus DYS570) may each be provided at a concentration of between about 0.01 and 1 µM;

SEQ ID NOS:19 and 20 (the primer pair able to amplify the RM Y-STR located at locus DYS576) may each be provided at a concentration of between about 0.01 and 1 µM;

SEQ ID NOS:21 and 22 (the primer pair able to amplify the RM Y-STR located at locus DYS612) may each be provided at a concentration of between about 0.01 and 1 µM;

SEQ ID NOS:23 and 24 (the primer pair able to amplify the RM Y-STR located at locus DYS626) may each be provided at a concentration of between about 0.01 and 1 µM; and SEQ ID NOS:25 and 26 (the primer pair able to amplify the RM Y-STR located at locus DYS627) may each be provided at a concentration of between about 0.01 and 1 µM.

Optimisation of the concentrations at which the primers are used further heightens the benefits provided by the methods of the invention. In suitable embodiments, concentrations for the various primers may be selected from the group set out below:

SEQ ID NOS:1 and 2 (the primer pair able to amplify the RM Y-STR located at locus DYF387S1) may each be provided at a concentration of 0.05 µM;

SEQ ID NOS:3 and 4 (the primer pair able to amplify the RM Y-STR located at locus DYF399S1) may each be provided at a concentration of 0.07 µM;

SEQ ID NOS:5 and 6 (the primer pair able to amplify the RM Y-STR located at locus DYF403S1a/b) may each be provided at a concentration of 0.20 µM;

SEQ ID NOS:7 and 8 (the primer pair able to amplify the RM Y-STR located at locus DYF404S1) may each be provided at a concentration of 0.10 µM;

SEQ ID NOS:9 and 10 (the primer pair able to amplify the RM Y-STR located at locus DYS449) may each be provided at a concentration of 0.06 µM;

SEQ ID NOS:11 and 12 (the primer pair able to amplify the RM Y-STR located at locus DYS518) may each be provided at a concentration of 0.08 µM;

SEQ ID NOS:13 and 14 (the primer pair able to amplify the RM Y-STR located at locus DYS526a/b) may each be provided at a concentration of 0.40 µM;

SEQ ID NOS:15 and 16 (the primer pair able to amplify the RM Y-STR located at locus DYS547) may each be provided at a concentration of 0.20 µM;

SEQ ID NOS:17 and 18 (the primer pair able to amplify the RM Y-STR located at locus DYS570) may each be provided at a concentration of 0.04 µM;

SEQ ID NOS:19 and 20 (the primer pair able to amplify the RM Y-STR located at locus DYS576) may each be provided at a concentration of 0.03 µM;

SEQ ID NOS:21 and 22 (the primer pair able to amplify the RM Y-STR located at locus DYS612) may each be provided at a concentration of 0.07 µM;

SEQ ID NOS:23 and 24 (the primer pair able to amplify the RM Y-STR located at locus DYS62) may each be provided at a concentration of 0.04 µM; and SEQ ID NOS:25 and 26 (the primer pair able to amplify the RM Y-STR located at locus DYS627) may each be provided at a concentration of 0.33 µM.

In a particularly preferred embodiment, a method of the invention uses each of the primers referred to above, and each is provided at the concentration referred to above.

This recognition of the benefits of controlling and optimising primer concentrations also lends itself to use in the kits of the invention. In a suitable embodiment of a kit of the invention the primers are provided in sufficient amounts such that, on dilution with a known volume of a diluent to produce a PCR reaction mixture, the concentrations of the primers lie within the ranges set out above.

In suitable embodiments the kits of the invention comprise primers in amounts such that, when the kit is used to produce a working PCR reaction mixture, the primers are present at the optimised concentration values set out above.

In preferred embodiments all of the primers of SEQ ID NOS:1 to 26 may be provided in amounts sufficient to provide the preferred concentration ranges, or optimised concentration values, set out above.

PCR will typically be undertaken in a suitable PCR buffer, of the sort well known to those skilled in the art. A suitable buffer (such as that provided with the DNA polymerase Platinum® Taq) may constitute between 25% and 75% of the total volume of PCR reaction.

PCR requires the presence of deoxyribonucleotides (dGTP, dATP, dTTP, and dCTP), and these may be provided in the methods of the invention at a concentration of approximately 220 µM.

The PCR used in the methods of the invention may take place in the presence of magnesium chloride ($MgCl_2$), which may optionally be provided at a concentration of approximately 1.65 mM.

Some, or all, of these constituents may be provided in the kits of the invention. Accordingly, a kit of the invention may further comprise one or more of the following constituents:

PCR Buffer. The PCR buffer may be provided in the form of an appropriate concentrate that is subsequently diluted in order to yield a working solution.

$MgCl_2$. This may be provided in an amount sufficient that when a working PCR solution is produced the $MgCl_2$ is present at a concentration of 1.65 mM.

Deoxyribonucleotides. These may be provided in an amount sufficient that when a working PCR solution is produced the deoxyribonucleotides are present at a concentration of approximately 220 µM.

The inventors have investigated the upper limits of various constituents that may be present in a PCR mixture, without affecting the suitability of the methods of the invention to co-amplify RM Y-STRs. They found that the methods of the invention are effective event when they comprise one or more of the following constituents:

EDTA at a concentration of up to 2 mM.

Haematin at a concentration of up to 500 µM.

Humic acid at a concentration of up to 100 µM.

Tannic acid at a concentration of up to 200 ng/µl.

$MgCl_2$ at a concentration of up to 20 mM.

Accordingly, it may be desired to maintain the amounts of one or all of these constituents present in the reaction mixture at or below the values set out in the preceding paragraph.

A suitable thermal cycler protocol for PCR that may be used in the methods of the invention comprises the following steps:

One cycle of approximately ten minutes at 95° C.;

Twelve cycles comprising: 30 seconds at 94° C.; followed by 45 seconds at an annealing temperature of between 50 and 60° C.; followed by one minute at 72° C.;

Between eighteen and twenty cycles comprising: 30 seconds at 94° C.; followed by 45 seconds at an annealing temperature of between 50 and 60° C.; followed by one minute at 72° C.;

One cycle of approximately 45 minutes at 60° C.

In a suitable embodiment, the first annealing temperature (used for twelve cycles) is 58° C. This value is associated with improved effectiveness of the PCR.

In an additional or alternative embodiment the second annealing temperature (used for between eighteen and twenty cycles) is 55° C. This value is also associated with improved effectiveness of the PCR.

The reason mixture can then be maintained at a temperature of up to approximately 15° C. for an indefinite period of time.

A wide range of DNA polymerases may be used in the methods or kits of the invention. A number of commercially available DNA polymerases that may be used are provided in the following paragraphs, by way of example.

In a suitable embodiment, a method of the invention may utilise Platinum® Taq DNA polymerase as the polymerase. For guidance, approximately 0.15 units of Platinum® Taq DNA polymerase is sufficient for use in a 15 µl PCR reaction mixture. The PCR cycle provided by way of illustration above is suitable for use in embodiments that make use of Platinum® Taq.

Alternative DNA polymerases that may be utilised in the methods or kits of the invention include Amplitaq Gold, Thermoprime Taq, OmniTaq, and Fusion Hi Fidelity DNA Polymerase, which may constitute a preferred polymerase. Any of these DNA polymerases are able to co-amplify RM Y-STRs when used with the primers of SEQ ID NOS:1 to 26, and so may be utilised in the methods or kits of the invention. Concentrations of the primers and other PCR reaction constituents, along with details such as the temperatures and times of the PCR cycle, may be altered as necessary in such embodiments.

The kits and methods of the invention allow allelic determination in respect of Y-STRs to be practiced using small samples of DNA. Merely by way of example, the inventors have found that accurate determination of alleles of Y-STRs can be achieved in samples containing as little as 62.5 pg of DNA. The lower level of DNA that may be present in a sample while still allowing accurate determination of alleles of Y-STRs by the kits and methods of the invention may be less than this figure. Certainly samples comprising at least 62.5 pg of DNA are able to be used.

The kits and methods of the invention have been proven to work experimentally using sample sizes of up to 3 ng of DNA. It is expect that both the methods and kits of the invention will continue to be effective using much higher sample sizes if required.

Figure 6:
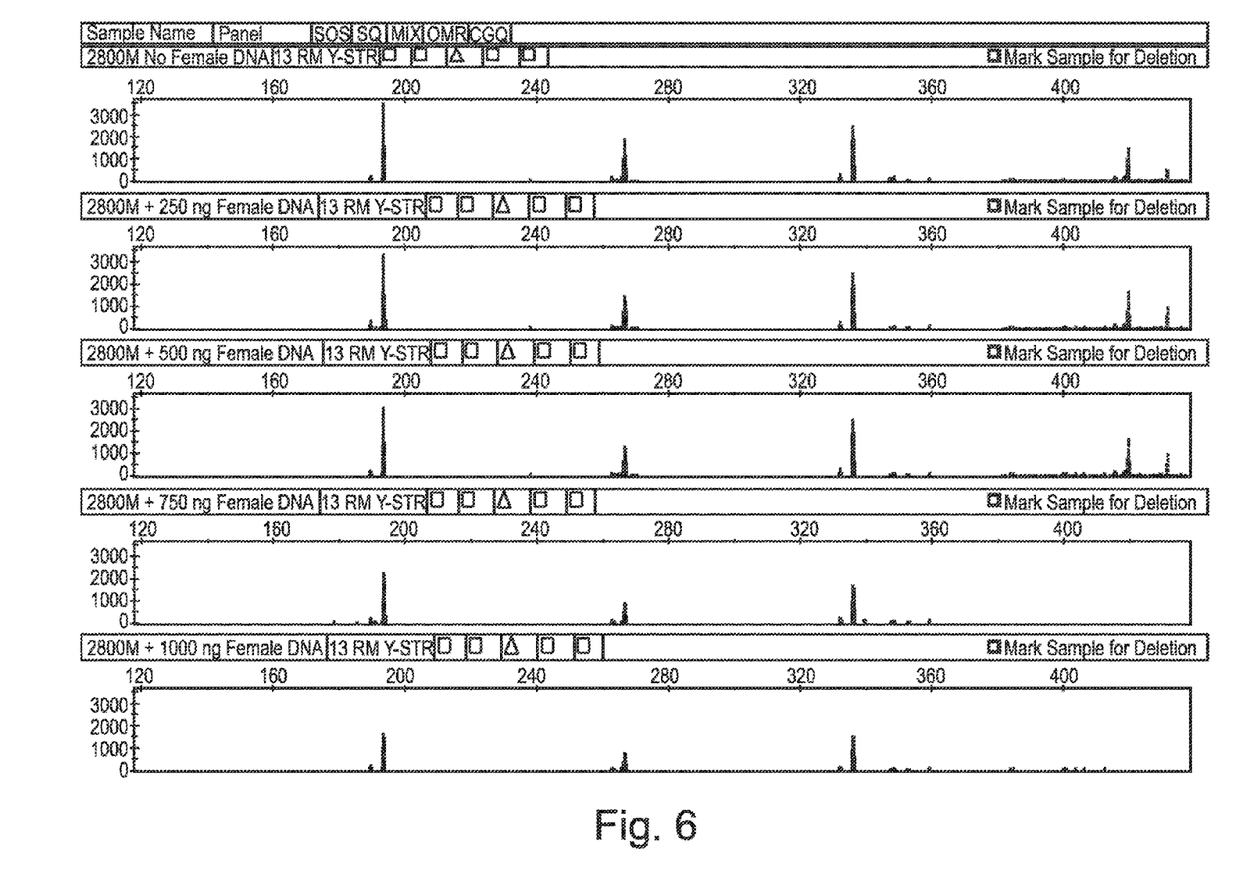
FIG. 6 illustrates that the methods and kits of the invention are able to co-amplify thirteen RM Y-STRs when 1 ng of male template DNA was mixed with up to 1 pg female DNA template.

Furthermore, the kits and methods of the invention allow allelic determination in respect of Y-STRs to be undertaken in samples comprising both male and female DNA, in which male DNA (including the Y chromosome) is only a very small proportion of the total. For example, the results set out in FIG. 6 illustrate that the methods and kits of the invention are able to co-amplify RM Y-STRs from male DNA present in a quantity one thousandth that of the female DNA present.

The kit of the first aspect of the invention may comprise a set of primers in which each of SEQ ID NOS:1 to 26 are present, and optionally one or more further primers. The kit of the first aspect of the invention may comprise a set of primers in which each of SEQ ID NOS:1 to 26 is present, and one, more than one, or all of the primers comprises additional nucleotides not set out in the sequences of Table 2.

Kits of the invention may also comprise instructions as to how methods utilising the kits of the invention may be practiced. Kits of the invention may comprise instructions as to how alleles of RM Y-STRs in a sample of interest may be determined.

The methods and kits of the invention may be practiced in any suitable apparatus in which PCR may be achieved. Merely by way of example, the methods of the invention may be practiced using, or the kits of the invention used in conjunction with, a DNAscan Rapid DNA Analysis System (GE) and a DNAscan BioChipSet Cassette.

Methods of the invention involve comparing the PCR products with reference values representative of different alleles of the RM Y-STRs to determine the alleles present in the sample. Reference values representative of different alleles of the RM Y-STRs being investigated may be provided in a number of different forms. Typically, suitable reference values may be provided in the form of an allelic ladder.

Comparison of the PCR products may be undertaken in any suitable manner compatible with the nature of the reference values that have been selected. For example, in the case that the reference values are provided in the form of an allelic ladder (in the manner contemplated above), then a sample of the allelic ladder can be processed in parallel with the PCR products. For example, if the PCR products are to be investigated using a DNA sequencer, then a sample of the allelic ladder may also be investigated in the same manner.

In a suitable embodiment a kit of the invention comprises information as to reference values of different alleles of the RM Y-STRs. In a suitable embodiment, this information is provided in the form of an allelic ladder.

The methods and kits of the invention allow determination of alleles of RM Y-STRs in a sample of interest. Allelic information regarding Y-STRs, and particularly RM Y-STRs, is of use in a range of contexts, not least forensic applications.

It will be appreciated that the methods of the invention in which alleles of Y-STRs in a sample of interest allow identification of an individual from whom that sample has been obtained. In such embodiments, the method of the invention may comprise not only comparing the PCR products with reference values representative of different alleles of the RM Y-STRs to determine the alleles present in the sample, but further comparing this information with information regarding the alleles present in an individual of interest (e.g. comparing the alleles present in the sample with the profile of alleles known to be possessed by a suspect or known offender).

In suitable embodiments of the methods or kits of the invention each primer pair is fluorescently labelled. Suitably at least one of the primers in a pair is fluorescently labelled by means of a fluorophore conjugated to the primer. Merely by way of example, at least one of the primers in a pair may be fluorescently labelled by means of a fluorophore covalently bonded to the primer.

Suitable fluorophores with which the primers may be labelled include those selected from the group consisting of: FAM; Yakima yellow; ATT0550; and ATT0565.

Figure 1:
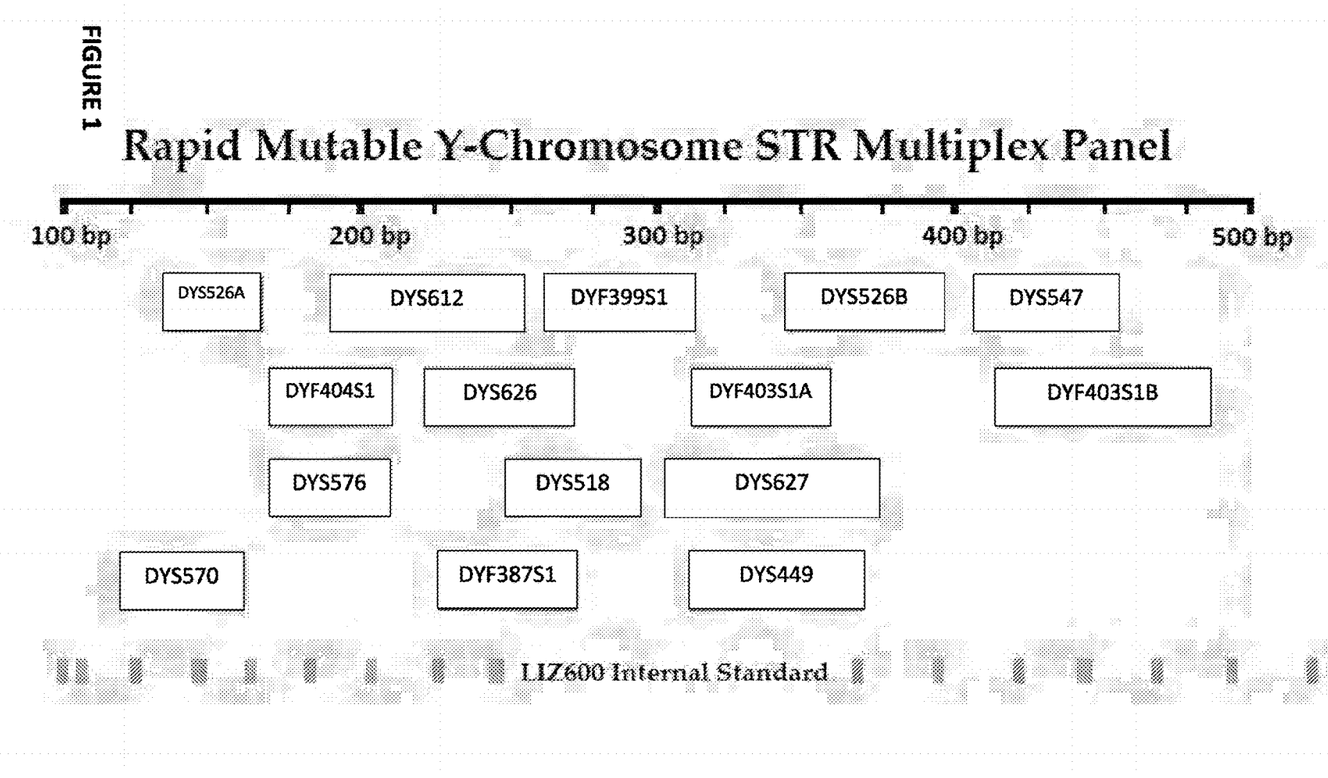
FIG. 1 illustrates PCR product size ranges for the RM Y-STRs amplified by the primer pairs set out in SEQ ID NOS:1 to 26, and also details of the fluorophores incorporated in these products by virtue of their associations with the primers.

A suitable arrangement for the labelling of primer pairs (and hence the PCR products comprising the RM Y-STR that they amplify) with fluorophores is illustrated in FIG. 1. The allelic ranges of different loci were ascertained. Same colour fluorescent labels were next selected for loci that were relatively distant from one another. This ensures that there is no overlap of the allelic ranges of adjacent loci in a particular colour panel. The same process was repeated for each panel and four colour panels were developed. The loci are well spaced in the current system and also provide for a possibility of substitution of the fluorescent panels.

EXAMPLES

Validation of the methods and kits of the invention was carried out using the methods and kits to co-amplify thirteen RM Y-STR markers in 600 male samples from the UAE population. Sensitivity, specificity, and ability to function in mixed samples were tested, along with discrimination capacity.

Briefly, 600 consented samples of unrelated male individuals form the UAE, comprising three major native groups (Bedouin Arabs, Urban Arabs, and Hajar Mountain Arabs) were collected from donors at Dubai Health Authority and Dubai Police General Head Quarters as blood stains on FTS cards. DNA was either extracted and quantified, or amplified using 1.2 mm FTA punch.

The 600 samples were genotyped and statistics were determined as follows:

Haplotype diversity was calculated according to the equation $(n/n-1)(1-f_i^2)$ where n is the number of samples and f is the frequency of the ith haplotype in the population Discrimination capacity was calculated as (number of different haplotypes/total number of haplotypes).

The results are shown in Table 1:

| Forensic parameter | Bedouin Arabs | Urban Arabs | Hajar Mountain Arabs | Total |
|---|---|---|---|---|
| Number of individuals | 200 | 200 | 200 | 600 |
| Number of haplotypes | 199 | 200 | 199 | 598 |
| Haplotype diversity | 0.99985 | 1.00000 | 0.99985 | 0.99997 |
| Discrimination capacity (%) | 99.5 | 100 | 99.5 | 99.7 |

The haplotype diversity that may be determined using the methods or kits of the invention was compared with that which may be determined using commercially available genotyping products, specifically the PowerPlex® Y23 system available from Promega, and the Yfiler® kit available from Life Technologies, Inc.

The results of this comparison are set out in Table 3:

| Product | Number of samples | Haplotype diversity determined |
|---|---|---|
| Method or kit of the invention | 600 | 0.99997 |
| Yfiler ® | 164 | 0.965 |
| PowerPlex ® Y23 | 164 | 0.900 |

From these results it can be seen that the capabilities of the methods and kits of the invention compare favourably to those of products that are already commercially available.

Figure 2:
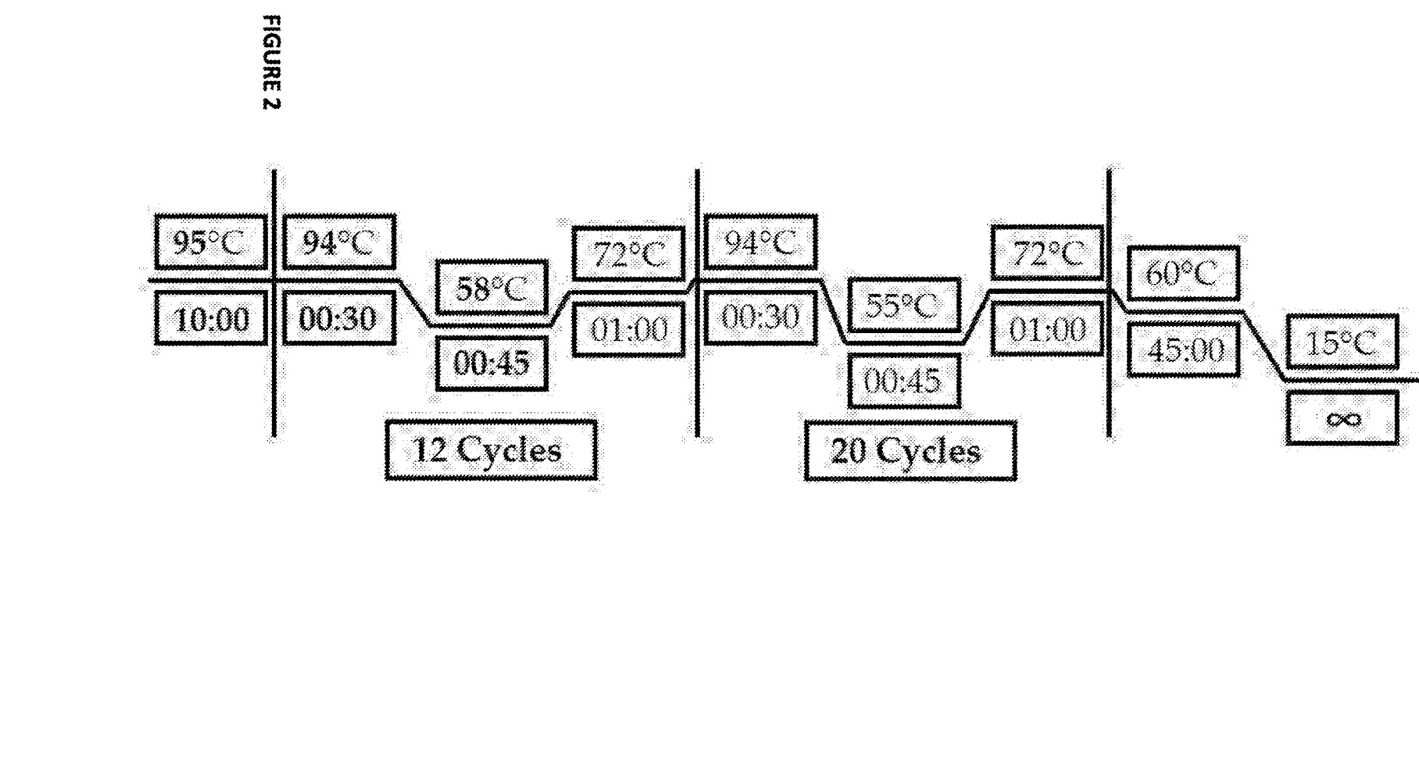
FIG. 2 illustrates an optimized amplification cycle for use in the methods of the invention. Incorporation of the RM Y-STR primer pairs set out in Table 2 with optimised concentration of primers and Platinum PCR Master Mix achieved robust genotyping data under these conditions.

FIGS. 1 and 2 respectively show the arrangement of fluorescent dyes with primers (and hence the primers' PCR products comprising the RM Y-STRs), and the optimised PCR cycle used in these exemplary methods of the invention. In this embodiment, amplification products of those RM Y-STRs in the upper row (DYS526A, DYS612, DYF399S1, DYS526B, and D7S547) are labelled with a single colour of fluorophore (e.g. blue), while those in the second row (DYF404S1, DYS626, DYF403S1A, and DYF403S1B) are labelled in with a different colour of fluorophore (e.g. green). Amplification products of the RM Y-STRs in the third row (DYS576, DYS518, and DYS627) are labelled with a third colour of fluorophore (e.g. yellow), while those in the bottom row (DYS570, DYF387S1, and DYS449) are labelled in with a fourth colour of fluorophore (e.g. red).

Figure 3:
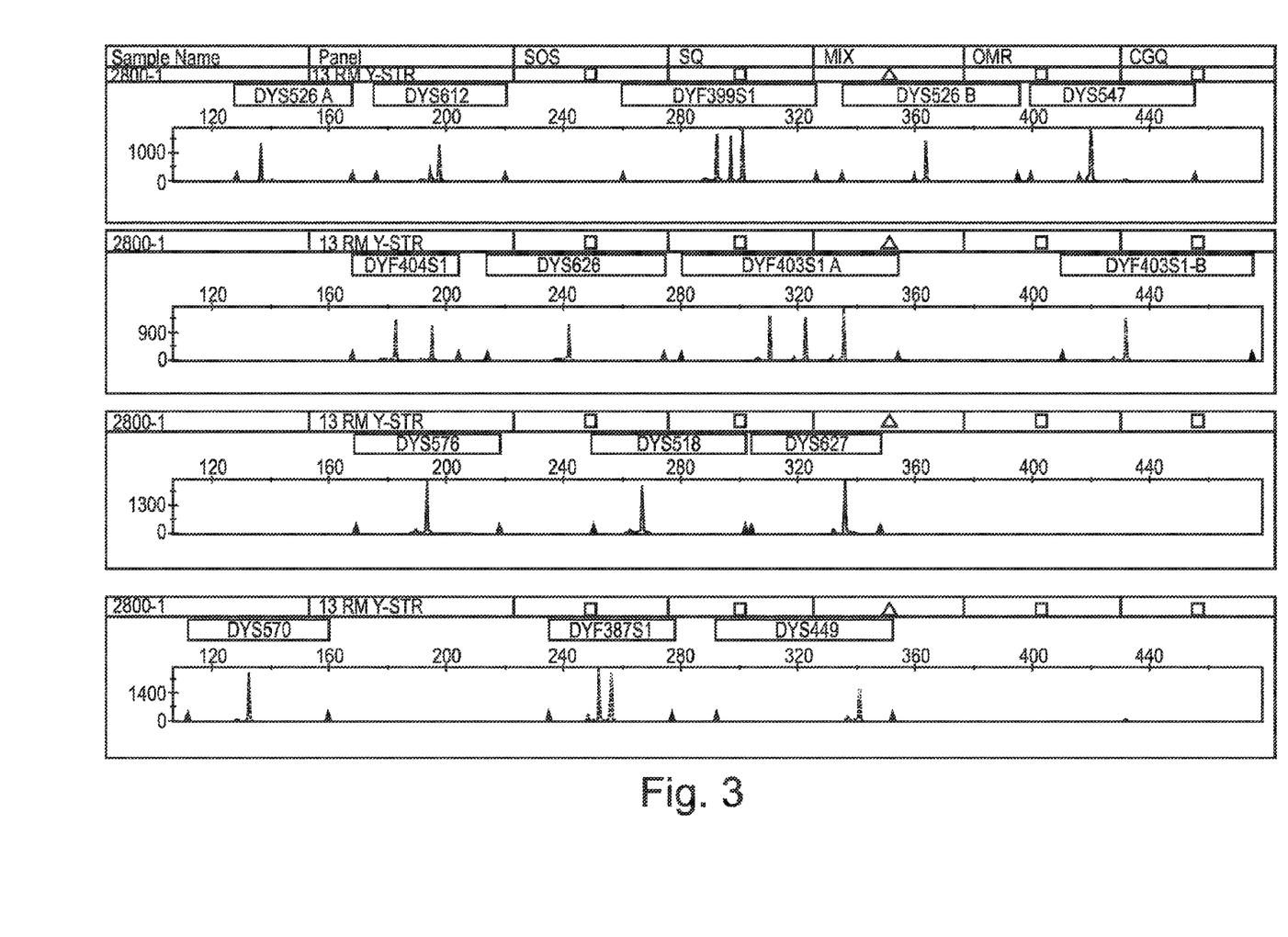
FIG. 3 illustrates the results of analysis of control male DNA investigated using a method of the invention, and analysed with a ABI 3500 Genetic Analyser.

Results are shown in FIG. 3, which illustrates the Y-STR profiles generated for a control male DNA using an ABI 3500 Genetic Analyser.

Figure 4:
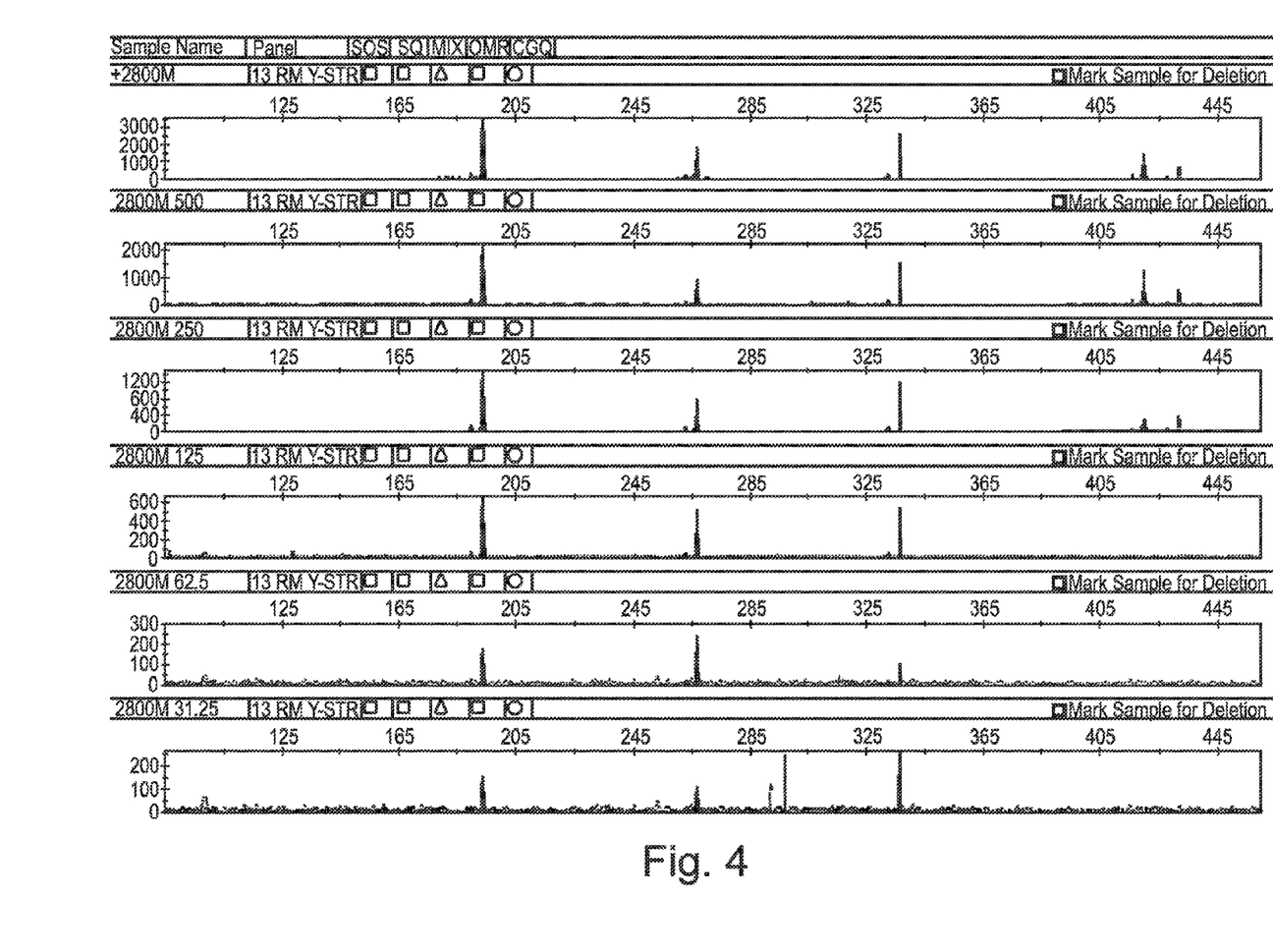
FIG. 4 shows a series of results indicating the sensitivity of the methods of the invention, and illustrating the low DNA sample sizes that can be used effectively.
Figure 5:
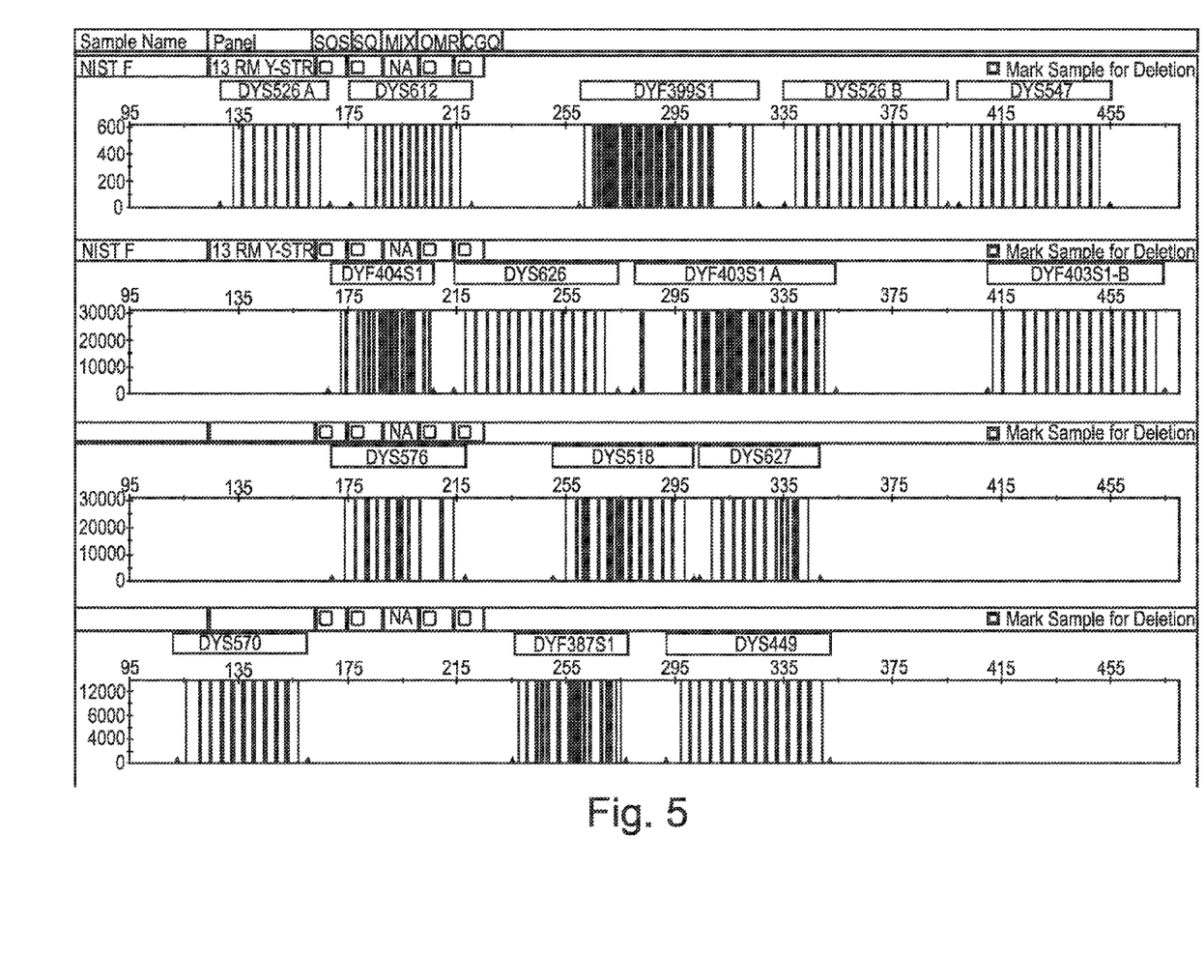
FIG. 5 illustrates the specificity of the methods and kits of the invention, and demonstrates that no template amplification was observed when exclusively female DNA was used as a control sample.

The results of a mini-validation are shown in FIGS. 4 to 6. FIG. 4 illustrates the sensitivity of the methods and kits of the invention, which were able to successfully co-amplify thirteen RM Y-STRs when the initial DNA sample was as low as 62.5 pg. FIG. 5 illustrates the specificity of the methods and kits of the invention, which did not cause template amplification when used to perform PCR on solely female DNA, even up to an input level of 10 ng (far higher than the 62.5 pg sample of male DNA successfully co-amplified in FIG. 4). FIG. 6 shows that the methods and kits of the invention are able to successfully co-amplify RM Y-STRs from mixtures of male and female DNA even when the ratio of male:female DNA is 1:1000.

Figure 7:
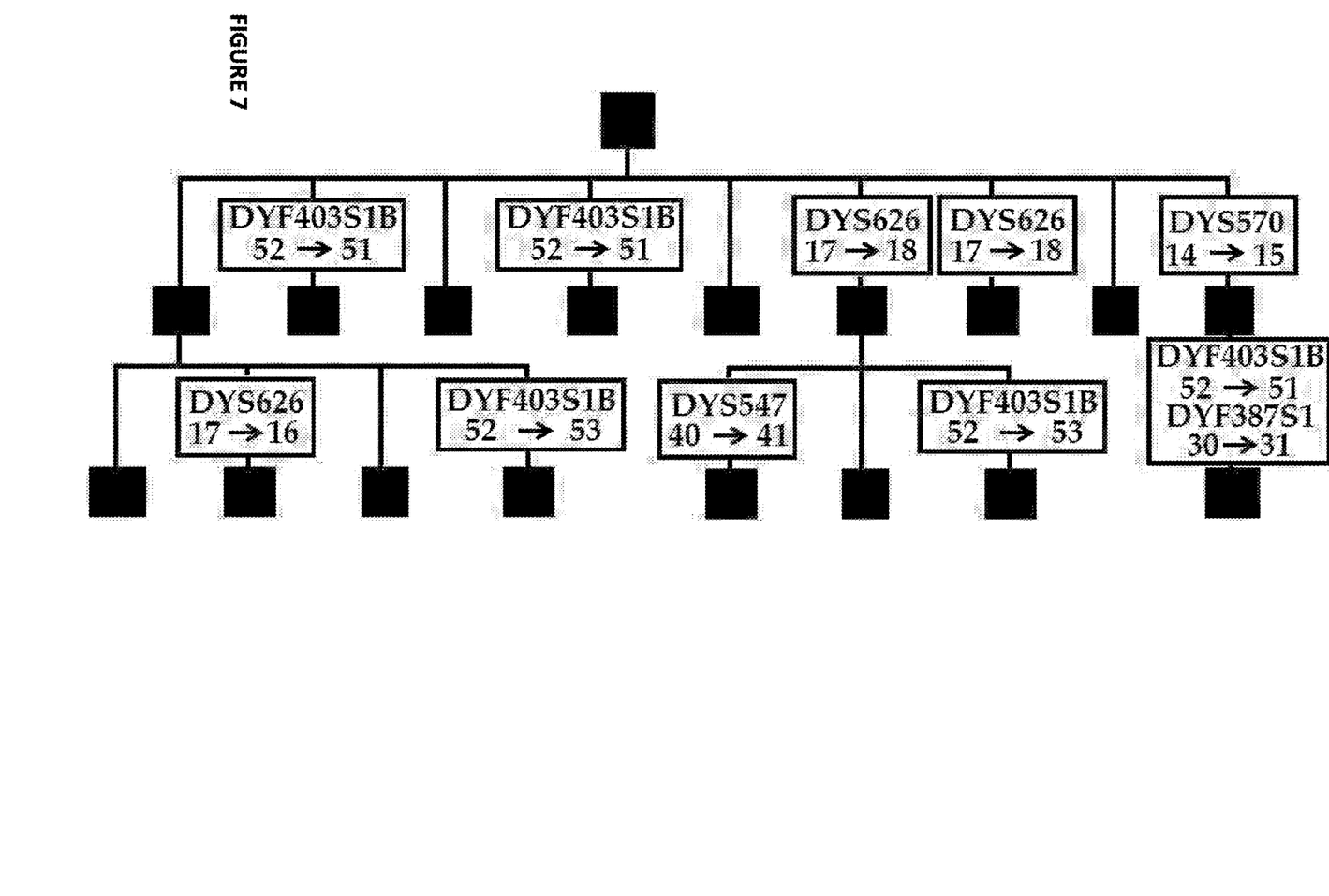
FIG. 7 represents mutation pattern analysis of the RM Y-STRs in a typical United Arab Emirates (UAE) family.

Finally, FIG. 7 represents mutation pattern analysis for the RM Y-STRs in a typical UAE family.

The ability of the methods and kits of the invention to function effectively and with requisite sensitivity in the presence of various factors frequently found in the context of forensic samples is highly important to their practical application.

As set out above, the inventors have determined that the methods and kits of the invention were able to successfully determine the alleles of RM Y-STRs in samples comprising as little as 62.5 picograms of male DNA. Successful determination of alleles can be achieved from such small starting samples even in the presence of up to 10 nanograms of female DNA. Indeed, the presence of up to 3000 nanograms of female DNA in a sample comprising mixed male and female DNA did not prevent the successful determination of alleles of RM Y-STRs present in the male DNA sample.

Furthermore, the inventors determined that methods and kits of the invention allowed successful determination of the alleles of RM Y-STRs in samples of male DNA even in the presence of various compounds that are commonly found in forensic samples, but which are known to inhibit PCR. In particular, the inventors found that the methods and kits of the invention allowed successful determination of alleles of RM Y-STRs in samples containing hematin (at a concentration of 100 nanograms per microliter), humic acid (at a concentration of 100 nanograms per microliter), or tannic acid (at a concentration of 200 nanograms per microliter). These results demonstrate that, while highly sensitive and selective, the methods and kits of the invention are also robust in the presence of contaminants, illustrating their suitability for practical use in the field of forensic science.

TABLE 2

Sequence information

| Locus | Forward primer | Reverse primer |
|---|---|---|
| DYF387S1 | (Optional ATTO565 fluorophore)- ACAGAGCTAGATTCCATTTTACCC (SEQ ID NO: 1) | GCCACAGTGTGAGA AGTGTGA (SEQ ID NO: 2) |
| DYF399S1 | (Optional 6-FAM fluorophore)- GGGTTTTCACCAGTTTGCAT (SEQ ID NO: 3) | CCATGTTTTGGGAC ATTCCT (SEQ ID NO: 4) |
| DYF403S1a/b | (Optional YakimaYellow fluorophore)- CAAAATTCATGTGGATAATGAG (SEQ ID NO: 5) | ACAGAGCAGGATTC CATCTA (SEQ ID NO: 6) |
| DYF404S1 | (Optional YakimaYellow fluorophore)- GGCTTAAGAAATTTCAACGCATA (SEQ ID NO: 7) | CCATGATGGAACAA TTGCAG (SEQ ID NO: 8) |
| DYS449 | (Optional ATTO565 fluorophore)- TGGAGTCTCTCAAGCCTGTTC (SEQ ID NO: 9) | CCATTGCACTCTAG GTTGGAC (SEQ ID NO: 10) |
| DYS518 | (Optional ATTO550 fluorophore)- GGCAACACAAGTGAAACTGC (SEQ ID NO: 11) | TCAGCTCTTACCAT GGGTGAT (SEQ ID NO: 12) |
| DYS526a/b | (Optional 6-FAM fluorophore)- TCTGGTGAACTGATCCAAACC (SEQ ID NO: 13) | GGGTTACTTCGCCA GAAGGT (SEQ ID NO: 14) |

TABLE 2-continued

Sequence information

| Locus | Forward primer | Reverse primer |
|---|---|---|
| DYS547 | (Optional 6-FAM fluorophore)-TCCATGTTACTGCAAAATACAC (SEQ ID NO: 15) | TGACAGAGCATAAACGTGTC (SEQ ID NO: 16) |
| DYS570 | (Optional ATTO565 fluorophore)-CTGGCTGTGTCCTCCAAGTT (SEQ ID NO: 17) | GGCAACCTAAGCTGAAATGC (SEQ ID NO: 18) |
| DYS576 | (Optional ATTO550 fluorophore)-GTTGGGCTGAGGAGTTCAATC (SEQ ID NO: 19) | GGCAGTCTCATTTCCTGGAG (SEQ ID NO: 20) |
| DYS612 | (Optional 6-FAM fluorophore)-CCCCATGCCAGTAAGAATA (SEQ ID NO: 21) | GTGAGGGAAGGCAAAAGAAAA (SEQ ID NO: 22) |
| DYS626 | (Optional YakimaYellow fluorophore)-GCAAGACCCCATAGCAAAAG (SEQ ID NO: 23) | AAGAAGAATTTTGGGACATGTTT (SEQ ID NO: 24) |
| DYS627 | (Optional ATTO550 fluorophore)-CTAGGTGACAGCGCAGGATT (SEQ ID NO: 25) | GGATAATGAGCAAATGGCAAG (SEQ ID NO: 26) |

The invention claimed is:

1. A method of determining the alleles of rapidly mutating Y chromosome short tandem repeats (RM Y-STRs) in a sample of interest, the method comprising:
 providing a sample comprising DNA;
 contacting the sample with a set of 26 primers comprising SEQ ID NOs: 1 to 26;
 performing a single multiplex polymerase chain reaction (PCR) to co-amplify the RM Y-STRs at loci DYF 387S1; DYF399S1; DYF403S1a/b; DYF404S1; DYS449; DYS518; DYS526a/b; DYS547; DYS570; DYS576; DYS612; DYS626; and DYS627 if present in the DNA; and
 comparing the PCR products with an allelic ladder of the RM Y-STRs to determine the alleles present in the sample, wherein PCR is carried out using a Taq polymerase.

2. The method according to claim 1, wherein concentrations for the primers of SEQ ID NOS: 1 to 26 are selected from the group consisting of:
 SEQ ID NOS:1 and 2 each provided at a concentration of between about 0.01 and 1 µM;
 SEQ ID NOS:3 and 4 each provided at a concentration of between about 0.01 and 1 µM;
 SEQ ID NOS:5 and 6 each provided at a concentration of between about 0.01 and 1 µM;
 SEQ ID NOS:7 and 8 each provided at a concentration of between about 0.01 and 1 µM;
 SEQ ID NOS:9 and 10 each provided at a concentration of between about 0.01 and 1 µM;
 SEQ ID NOS:11 and 12 each provided at a concentration of between about 0.01 and 1 µM;
 SEQ ID NOS:13 and 14 each provided at a concentration of between about 0.01 and 1 µM;
 SEQ ID NOS:15 and 16 each provided at a concentration of between about 0.01 and 1 µM;
 SEQ ID NOS:17 and 18 each provided at a concentration of between about 0.01 and 1 µM;
 SEQ ID NOS:19 and 20 each provided at a concentration of between about 0.01 and 1 µM;
 SEQ ID NOS:21 and 22 each provided at a concentration of between about 0.01 and 1 µM;
 SEQ ID NOS:23 and 24 each provided at a concentration of between about 0.01 and 1 µM; and
 SEQ ID NOS:25 and 26 each provided at a concentration of between about 0.01 and 1 µM.

3. The method according to claim 2, wherein concentrations for the primers of SEQ ID NOS: 1 to 26 are selected from the group consisting of:
 SEQ ID NOS:1 and 2 each provided at a concentration of 0.05 µM;
 SEQ ID NOS:3 and 4 each provided at a concentration of 0.07 µM;
 SEQ ID NOS:5 and 6 each provided at a concentration of 0.20 µM;
 SEQ ID NOS:7 and 8 each provided at a concentration of 0.10 µM;
 SEQ ID NOS:9 and 10 each provided at a concentration of 0.06 µM;
 SEQ ID NOS:11 and 12 each provided at a concentration of 0.08 µM;
 SEQ ID NOS:13 and 14 each provided at a concentration of 0.40 µM;
 SEQ ID NOS:15 and 16 each provided at a concentration of 0.20 µM;
 SEQ ID NOS:17 and 18 each provided at a concentration of 0.04 µM;
 SEQ ID NOS:19 and 20 each provided at a concentration of 0.03 µM;
 SEQ ID NOS:21 and 22 each provided at a concentration of 0.07 µM;
 SEQ ID NOS:23 and 24 each provided at a concentration of 0.04 µM; and
 SEQ ID NOS:25 and 26 each provided at a concentration of 0.33 µM.

4. The method according to claim 1, wherein the PCR is conducted using a thermal cycler protocol comprising the following steps:
 one cycle of approximately ten minutes at 95° C.;
 twelve cycles comprising: 30 seconds at 94° C.; followed by 45 seconds at an annealing temperature of between 50 and 60° C.; followed by one minute at 72° C.;
 between eighteen and twenty cycles comprising: 30 seconds at 94° C.; followed by 45 seconds at an annealing temperature of between 50 and 60° C.; followed by one minute at 72° C.; and
 one cycle of approximately 45 minutes at 60° C.

5. The method according to claim 4, wherein the first annealing temperature is 58° C.

6. The method according to claim 4, wherein the second annealing temperature is 55° C.

7. A kit comprising a set of primers for the co-amplification of a group of rapidly mutating Y chromosome short tandem repeats (RM Y-STRs), wherein the set of primers comprises each of SEQ ID NOS: 1 to 26, and wherein at least one of the primers comprises a detectable label.

8. The kit according to claim 7, wherein the set of primers consists of SEQ ID NOS:1 to 26.

9. The kit according to claim 7, further comprising at least one of the following:
deoxyribonucleotides;
a DNA polymerase;
PCR buffer; or
an allelic ladder.

10. The kit according to claim 9, wherein the DNA polymerase comprises a Taq polymerase.

11. The kit of claim 7, wherein all of the primers comprise a detectable label.

* * * * *

SEQUENCE LISTING

<160> NUMBER OF SEQ ID NOS: 26

<210> SEQ ID NO 1
<211> LENGTH: 24
<212> TYPE: DNA
<213> ORGANISM: Artificial Sequence
<220> FEATURE:
<223> OTHER INFORMATION: Forward primer for locus DYF387S1

<400> SEQUENCE: 1
acagagctag attccatttt accc                                        24

<210> SEQ ID NO 2
<211> LENGTH: 21
<212> TYPE: DNA
<213> ORGANISM: Artificial Sequence
<220> FEATURE:
<223> OTHER INFORMATION: Reverse primer for locus DYF387S1

<400> SEQUENCE: 2
gccacagtgt gagaagtgtg a                                           21

<210> SEQ ID NO 3
<211> LENGTH: 20
<212> TYPE: DNA
<213> ORGANISM: Artificial Sequence
<220> FEATURE:
<223> OTHER INFORMATION: Forward primer for locus DYF399S1

<400> SEQUENCE: 3
gggttttcac cagtttgcat                                             20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for locus DYF399S1

<400> SEQUENCE: 4
ccatgttttg ggacattcct                                             20

<210> SEQ ID NO 5
<211> LENGTH: 22
<212> TYPE: DNA
<213> ORGANISM: Artificial Sequence

```
<220> FEATURE:
<223> OTHER INFORMATION: Forward primer for locus DYF403S1a/b

<400> SEQUENCE: 5
caaaattcat gtggataatg ag                                              22

<210> SEQ ID NO 6
<211> LENGTH: 20
<212> TYPE: DNA
<213> ORGANISM: Artificial Sequence
<220> FEATURE:
<223> OTHER INFORMATION: Reverse primer for locus DYF403S1a/b

<400> SEQUENCE: 6
acagagcagg attccatcta                                                 20

<210> SEQ ID NO 7
<211> LENGTH: 23
<212> TYPE: DNA
<213> ORGANISM: Artificial Sequence
<220> FEATURE:
<223> OTHER INFORMATION: Forward primer for locus DYF404S1

<400> SEQUENCE: 7
ggcttaagaa atttcaacgc ata                                             23

<210> SEQ ID NO 8
<211> LENGTH: 20
<212> TYPE: DNA
<213> ORGANISM: Artificial Sequence
<220> FEATURE:
<223> OTHER INFORMATION: Reverse primer for locus DYF404S1

<400> SEQUENCE: 8
ccatgatgga acaattgcag                                                 20

<210> SEQ ID NO 9
<211> LENGTH: 21
<212> TYPE: DNA
<213> ORGANISM: Artificial Sequence
<220> FEATURE:
<223> OTHER INFORMATION: Forward primer for locus DYS449

<400> SEQUENCE: 9
tggagtctct caagcctgtt c                                               21

<210> SEQ ID NO 10
<211> LENGTH: 21
<212> TYPE: DNA
<213> ORGANISM: Artificial Sequence
<220> FEATURE:
<223> OTHER INFORMATION: Reverse primer for locus DYS449

<400> SEQUENCE: 10
ccattgcact ctaggttgga c                                               21

<210> SEQ ID NO 11
<211> LENGTH: 20
<212> TYPE: DNA
<213> ORGANISM: Artificial Sequence
<220> FEATURE:
<223> OTHER INFORMATION: Forward primer for locus DYS518

<400> SEQUENCE: 11
ggcaacacaa gtgaaactgc                                                 20
```

<210> SEQ ID NO 12
<211> LENGTH: 21
<212> TYPE: DNA
<213> ORGANISM: Artificial Sequence
<220> FEATURE:
<223> OTHER INFORMATION: Reverse primer for locus DYS518

<400> SEQUENCE: 12
tcagctctta ccatgggtga t                                         21

<210> SEQ ID NO 13
<211> LENGTH: 21
<212> TYPE: DNA
<213> ORGANISM: Artificial Sequence
<220> FEATURE:
<223> OTHER INFORMATION: Forward primer for locus DYS526a/b

<400> SEQUENCE: 13
tctggtgaac tgatccaaac c                                         21

<210> SEQ ID NO 14
<211> LENGTH: 20
<212> TYPE: DNA
<213> ORGANISM: Artificial Sequence
<220> FEATURE:
<223> OTHER INFORMATION: Reverse primer for locus DYS526a/b

<400> SEQUENCE: 14
gggttacttc gccagaaggt                                           20

<210> SEQ ID NO 15
<211> LENGTH: 22
<212> TYPE: DNA
<213> ORGANISM: Artificial Sequence
<220> FEATURE:
<223> OTHER INFORMATION: Forward primer for locus DYS547

<400> SEQUENCE: 15
tccatgttac tgcaaaatac ac                                        22

<210> SEQ ID NO 16
<211> LENGTH: 20
<212> TYPE: DNA
<213> ORGANISM: Artificial Sequence
<220> FEATURE:
<223> OTHER INFORMATION: Reverse primer for locus DYS547

<400> SEQUENCE: 16
tgacagagca taaacgtgtc                                           20

<210> SEQ ID NO 17
<211> LENGTH: 20
<212> TYPE: DNA
<213> ORGANISM: Artificial Sequence
<220> FEATURE:
<223> OTHER INFORMATION: Forward primer for locus DYS570

<400> SEQUENCE: 17
ctggctgtgt cctccaagtt                                           20

<210> SEQ ID NO 18
<211> LENGTH: 20
<212> TYPE: DNA
<213> ORGANISM: Artificial Sequence
<220> FEATURE:
<223> OTHER INFORMATION: Reverse primer for locus DYS570

```
<400> SEQUENCE: 18
ggcaacctaa gctgaaatgc                                               20

<210> SEQ ID NO 19
<211> LENGTH: 21
<212> TYPE: DNA
<213> ORGANISM: Artificial Sequence
<220> FEATURE:
<223> OTHER INFORMATION: Forward primer for locus DYS576

<400> SEQUENCE: 19
gttgggctga ggagttcaat c                                             21

<210> SEQ ID NO 20
<211> LENGTH: 20
<212> TYPE: DNA
<213> ORGANISM: Artificial Sequence
<220> FEATURE:
<223> OTHER INFORMATION: Reverse primer for locus DYS576

<400> SEQUENCE: 20
ggcagtctca tttcctggag                                               20

<210> SEQ ID NO 21
<211> LENGTH: 19
<212> TYPE: DNA
<213> ORGANISM: Artificial Sequence
<220> FEATURE:
<223> OTHER INFORMATION: Forward primer for locus DYS612

<400> SEQUENCE: 21
ccccatgcca gtaagaata                                                19

<210> SEQ ID NO 22
<211> LENGTH: 21
<212> TYPE: DNA
<213> ORGANISM: Artificial Sequence
<220> FEATURE:
<223> OTHER INFORMATION: Reverse primer for locus DYS612

<400> SEQUENCE: 22
gtgagggaag gcaaaagaaa a                                             21

<210> SEQ ID NO 23
<211> LENGTH: 20
<212> TYPE: DNA
<213> ORGANISM: Artificial Sequence
<220> FEATURE:
<223> OTHER INFORMATION: Forward primer for locus DYS626

<400> SEQUENCE: 23
gcaagacccc atagcaaaag                                               20

<210> SEQ ID NO 24
<211> LENGTH: 23
<212> TYPE: DNA
<213> ORGANISM: Artificial Sequence
<220> FEATURE:
<223> OTHER INFORMATION: Reverse primer for locus DYS626

<400> SEQUENCE: 24
aagaagaatt ttgggacatg ttt                                           23

<210> SEQ ID NO 25
```

```
<211> LENGTH: 20
<212> TYPE: DNA
<213> ORGANISM: Artificial Sequence
<220> FEATURE:
<223> OTHER INFORMATION: Forward primer for locus DYS627

<400> SEQUENCE: 25
ctaggtgaca gcgcaggatt                                               20

<210> SEQ ID NO 26
<211> LENGTH: 21
<212> TYPE: DNA
<213> ORGANISM: Artificial Sequence
<220> FEATURE:
<223> OTHER INFORMATION: Reverse primer for locus DYS627

<400> SEQUENCE: 26
ggataatgag caaatggcaa g                                             21
```